United States Patent [19]
Fenton

[11] Patent Number: 5,000,748
[45] Date of Patent: Mar. 19, 1991

[54] OSTOMY DRAINAGE RECEPTACLE

[75] Inventor: Leonard Fenton, Beachwood, Ohio

[73] Assignee: Marlen Manufacturing & Development Company, Bedford, Ohio

[21] Appl. No.: 61,018

[22] Filed: Jun. 12, 1987

Related U.S. Application Data

[63] Continuation of Ser. No. 815,518, Jan. 2, 1986, abandoned.

[51] Int. Cl.$^5$ .............................................. A61F 5/44
[52] U.S. Cl. ................................................. 604/340
[58] Field of Search .............................. 604/332–345; D24/51, 54, 56

[56] References Cited

U.S. PATENT DOCUMENTS

| | | | |
|---|---|---|---|
| 2,818,069 | 12/1957 | Fenton | 604/338 |
| 3,283,757 | 11/1966 | Nelsen | 604/334 |
| 3,295,145 | 1/1967 | Ericson | D24/54 |
| 4,387,713 | 6/1983 | Calanni | 604/336 |
| 4,561,858 | 12/1985 | Allen, Jr. et al. | 604/336 |

OTHER PUBLICATIONS

Catalog Cat. United Surgical Corp.; Largo, Fla. 33540, p. 10, 1968.

Primary Examiner—David J. Isabella
Attorney, Agent, or Firm—Pearne, Gordon, McCoy & Granger

[57] ABSTRACT

An ostomy drainage receptacle comprising a flexible pouch having a stoma-receiving opening therein. A mounting assembly surrounds the opening, the mounting assembly comprising a stiffly flexible mounting ring having a flat annular rim portion sealed to the opening and a convex dome portion having a central stoma-receiving opening therethrough. The thickness of the convex dome portion gradually increases in radial directions from the rim to the stoma-receiving opening so that the dome portion may flex upon application of the receptacle to the body for a more secure seal. The receptacle has a relatively wide upper portion to provide space for a relatively large stoma and the increased width also provides a large adhesive area for application to the body.

8 Claims, 3 Drawing Sheets

OSTOMY DRAINAGE RECEPTACLE

This is a continuation of application Ser. No. 815,518, filed on Jan. 2, 1986, now abandoned.

BACKGROUND OF THE INVENTION

This invention relates to ostomy drainage receptacles and, more particularly, to ostomy appliances comprising a flexible pouch or bag adapted to be attached to the body of a patient and receive discharge from the stoma of a patient after surgical procedures, such as colostomy, ileostomy, urostomy, and ureterostomy procedures.

In the art of ostomy appliances, considerable efforts have been devoted to providing a secure yet comfortable attaching arrangement for ostomy pouches against the human body surrounding the stoma. With the development of more secure adhesives and lighter weight pouches, many ostomy patients are employing disposable pouches which are secured to the stoma area by an adhesive rather than the more traditional but comparatively uncomfortable strap or harness arrangement.

It has long been recognized that a rigid convex mounting ring or stoma plate or face plate presents a superior surface for adhesively securing a pouch to the human body adjacent to a stoma. This concept has been almost universally applied to bag mounting rings supported by a harness or belt. Such an arrangement is shown, for example, in U.S. Pat. Nos. 2,784,718; 2,595,934; and 2,684,676. Self-supporting or beltless bags were initially provided with a flat adhesive surface to attach the bag to the body. Examples of such arrangements are shown in U.S. Pat. No. 3,897,780 and Reissue No. 29,453. As is recognized in U.S. Pat. No. 4,219,023, the flexible pouch or bag making up the ostomy structure is somewhat planar in the area adjacent the stoma and many times improper fit will cause the waste material to accumulate around the stoma opening of the ostomy receptacle, thereby leading to undesirable leakage and skin conditions. To overcome this problem, the patentee discloses a convex insert which has the ability to transform existing prior art ostomy receptacles of the type employing a flexible pouch having a circumscribing cushion or pad about the ostomy opening so as to convexly position the ostomy receptacle about the stoma having due regard for the contours of the human body at the stoma site.

While the arrangement shown in U.S. Pat. No. 4,219,023 advantageously adapts the flat body engaging portion of existing drainage bags to a configuration which more securely seals the drainage bag to the stoma opening, the arrangement requires a relatively complicated assembly step by the user.

SUMMARY OF THE INVENTION

This invention provides a drainage receptacle for a stoma having a mounting assembly which securely fastens the receptacle to the body in surrounding relationship to the stoma and which securely seals the mounted receptacle against seepage at the sealed juncture.

According to this invention, the receptacle comprises a flexible pouch defined by flat, flexible plastic walls sealed at their peripheries. The walls may be formed as double walls to provide a completely sealed air space between inner and outer walls of the pouch to extend the useful life of the pouch without sacrificing comfort. Such an arrangement is shown in U.S. Pat. No. 3,385,298. An opening is provided through one of said walls or doubled walls adjacent an upper portion of the pouch and a mounting assembly surrounds the opening. The mounting assembly comprises a stiffly flexible mounting ring having a flat, annular rim portion sealed to the periphery of the opening and a convex dome portion having a central stoma-receiving opening therethrough. The thickness of the convex dome portion gradually increases in radial directions from the rim to the stoma-receiving opening so that the dome may flex upon application to the body to exert a constant sealing pressure against the skin.

According to another aspect of this invention, the upper portion of the pouch has a bulb-shaped head which provides an excess of pouch wall material to accommodate slightly abnormal stoma protrusion. The bulbous or enlarged portion of the pouch may be provided with a wide band of adhesive to more securely fasten the bag to the body and to ensure that the flexure of the convex dome against the body will not result in the peeling of the adhesive away from the body.

According to a still further aspect of this invention, an annular sealing ring may surround the stoma opening in the mounting assembly to cushion the opening and minimize irritation which may be caused by the repeated application of adhesive to the body. The sealing ring may be a soft foam or may comprise an adhesive skin barrier.

DETAILED DESCRIPTION OF THE INVENTION

Figure 1:
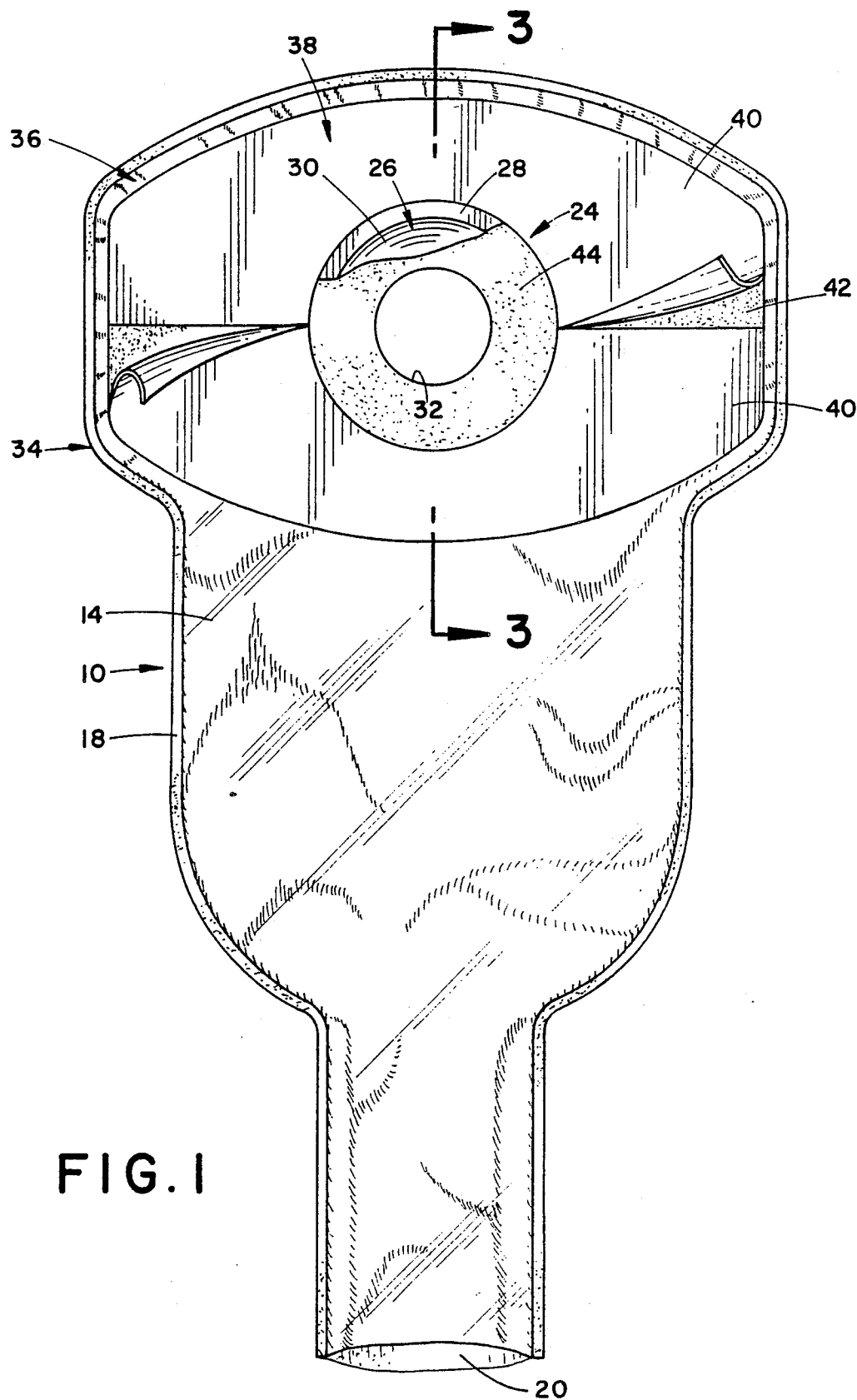
FIG. 1 is an elevational view of an ostomy drainage receptacle according to this invention, with portions broken away for clarity and with adhesive protecting webs partially peeled away for illustration purposes.

Referring now to the drawings, an ostomy drainage receptacle 10 is formed by a front wall 12 and a rear wall 14 which define a drainage chamber 16. The walls 12 and 14 may be formed from material such as polyethylene or other suitable thermoplastic materials, and may be single thickness walls or may be formed as double walls according to the teachings of U.S. Pat. No. 3,385,298 and, as is illustrated in the drawings. The walls 12 and 14 are heat-sealed about their peripheries to form a leakproof seal 18 and to define the chamber 16. If the walls 12 and 14 are double walls, the outermost wall may be formed from a non-woven, soft plastic material for added comfort to the user.

The walls 12 and 14 are unsealed at their bottom edges to provide an outlet drainage opening 20 for the chamber 16. During use, the opening 20 may be sealed by a suitable clip such as that shown in U.S. Pat. No. 4,460,359.

Figures 2, 3:
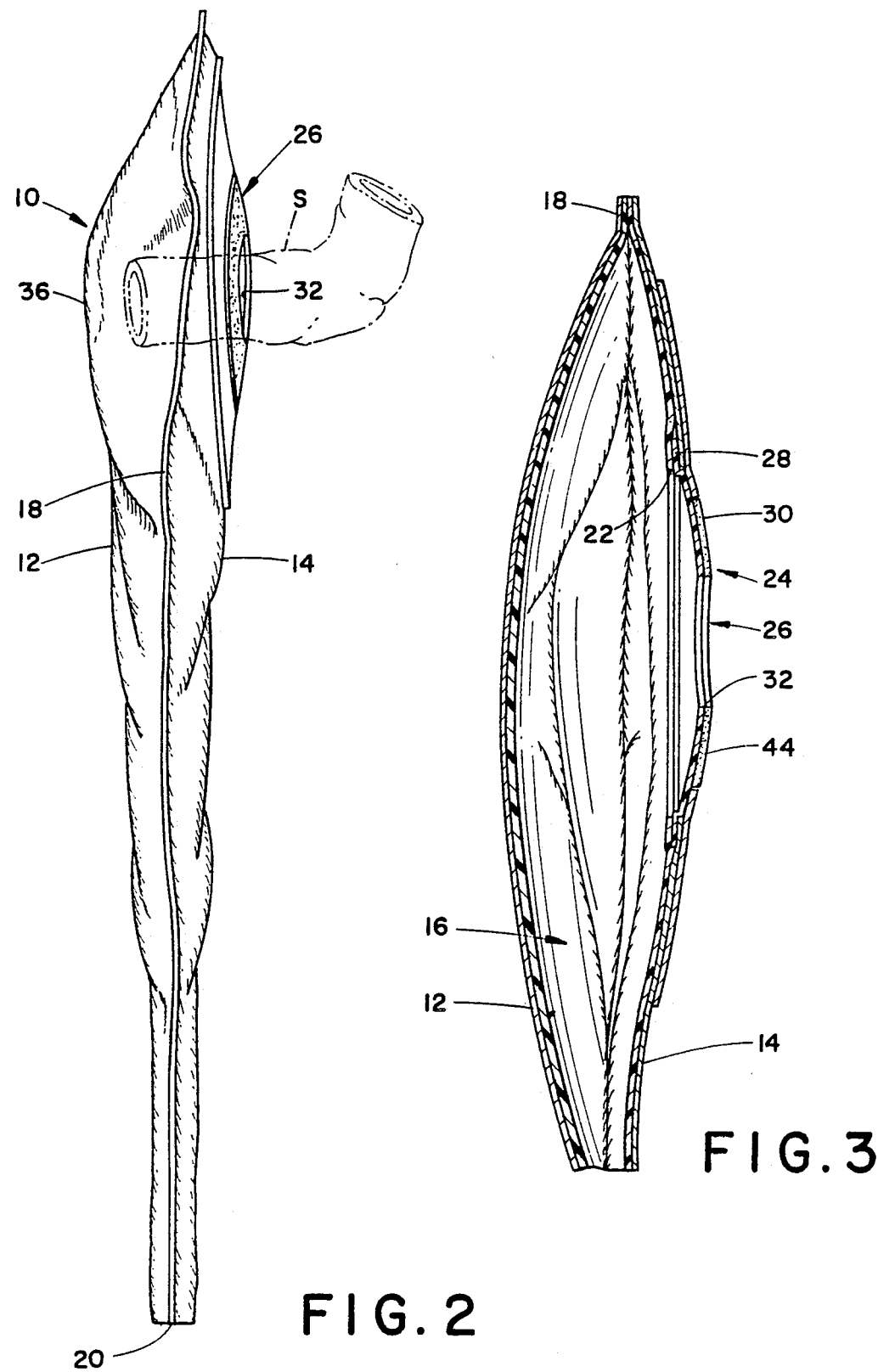
FIG. 2 is a side elevational view of the ostomy drainage receptacle illustrating the receptacle applied to the body and enclosing a stoma.
FIG. 3 is a cross-sectional view, the plane of the section being indicated by the line 3—3 in FIG. 1.

Adjacent an upper portion of the receptacle 10 is an opening 22 (FIG. 3) in the wall 14. A mounting assembly 24 is provided in the opening to surround a stoma S and includes a stiffly flexible mounting ring 26 having a flat annular rim portion 28 sealed to the opening 22 and a convex dome portion 30 with a stoma-receiving opening 32 therethrough.

Figure 4:
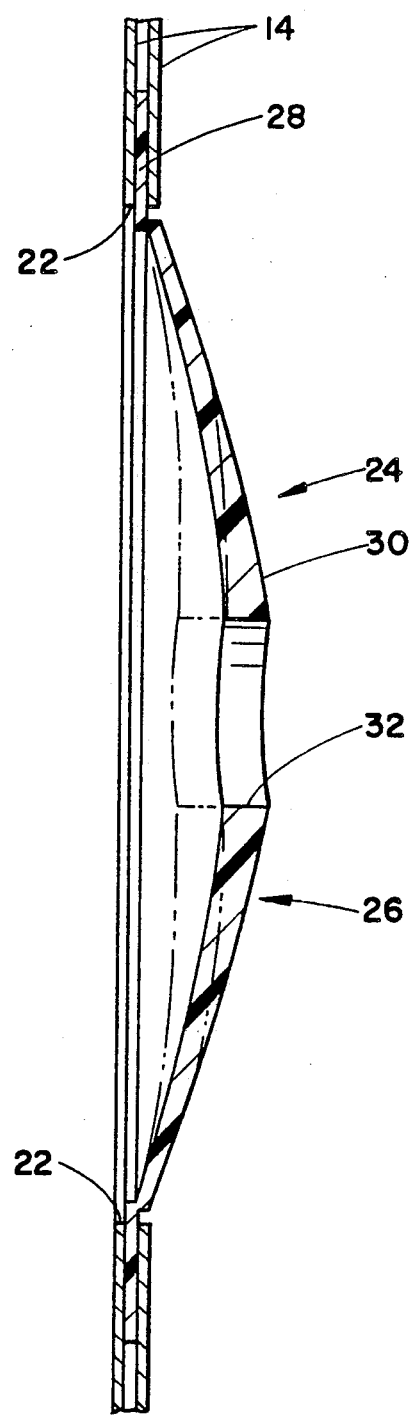
FIG. 4 is an enlarged, cross-sectional view illustrating the flexure of the mounting ring, stoma plate or face plate as it is applied to the body.

As may be seen most clearly in FIG. 4, the rim portion 28 has a uniform thickness and the dome portion 30 increases in radial directions from the thickness of the rim 28 to the stoma-receiving opening 32. This construction permits the dome portion 30 to flex, as is illustrated in phantom outline in FIG. 4, upon application of the receptacle 10 to the body and continuously bias the opening 32 against the body for a proper seal.

As may be seen in FIG. 1, the upper portion 34 of the bag has a bulbous or enlarged shape. The enlarged shape provides extra material 36 (FIG. 2) to accommodate unusually long stoma protrusions. The portion 34 also provides an enlarged surface area on the wall 14 for the application of a relatively large adhesive strip 38. The adhesive strip 38 is a double-faced adhesive adhered to the wall 14, and having protective release webs 40 to cover the body-engaging adhesive 42 prior to application. The adhesive 42 may extend to the perimeter of the opening 32 to directly engage the wearer's skin up to the stoma opening. More desirably, however, and as is illustrated, a cushioning pad 44 may cover the convex portion 30 of the mounting ring 26. The cushioning pad 44 may be made from a gumlike sealing composition, such as natural rubber impregnated with a water-soluble or swellable hydrocolloid. Such a composition is set forth in U.S. Pat. No. 3,339,546. A release liner (not shown) may be provided over the pad 44 to protect the pad prior to use.

Although the preferred embodiment of this invention has been shown and described, it should be understood that various modifications and rearrangements of the parts may be resorted to without departing from the scope of the invention as disclosed and claimed herein.

I claim:

1. An ostomy drainage receptacle comprising a flexible pouch defined by drainage chamber defining walls, means defining an opening in one of said walls adjacent an upper portion of said pouch, and a mounting assembly surrounded by said opening in one of said walls adjacent said upper portion of said pouch, said mounting assembly comprising a stiffly flexible mounting ring having a flat annular rim portion defining its outer periphery sealed to said opening and a convex dome portion having a central stoma-receiving opening therethrough, said convex dome portion being defined by a convex outer surface and a concave inner surface, each said surface extending from said flat annular rim portion and terminating at said stoma-receiving opening, the thickness of said convex dome portion gradually increasing in radial directions from said rim to said stoma-receiving opening.

2. An ostomy drainage receptacle according to claim 1, wherein said thickness gradually increases in all radial directions.

3. An ostomy drainage receptacle according to claim 1, wherein said mounting assembly includes adhesive means adhered to at least a portion of said convex dome and having a body-engaging portion for securing said flexible pouch to the body and sealing the stoma-receiving opening about a stoma.

4. An ostomy receptacle according to claim 1, wherein said pouch includes an intermediate body portion and a relatively narrow lower drainage spout, and wherein the upper portion of the pouch is wider than the intermediate body portion of the pouch to provide additional room for a protruding stoma.

5. An ostomy receptacle according to claim 4 wherein said upper portion of said pouch is substantially covered with said adhesive means.

6. An ostomy receptacle according to claim 1, wherein a soft pliable sealing ring is adhered to said convex dome portion and wherein said ring is adapted to form a seal against the body around the stoma.

7. An ostomy receptacle according to claim 1, wherein said pouch has a lower reclosable drainage opening.

8. An ostomy drainage receptacle comprising a flexible pouch defined by drainage chamber defining walls, means defining an opening in one of said walls adjacent an upper portion of said pouch, said upper portion being wider than the remainder of the pouch to provide additional room for a protruding stoma, a mounting assembly surrounded by said opening in one of said walls adjacent said upper portion of said pouch, said mounting assembly comprising a stiffly flexible mounting ring having a flat annular rim portion defining its outer periphery and a convex dome portion having a central stoma-receiving opening therethrough, said convex dome portion being defined by a convex outer surface and a concave inner surface terminating at said stoma-receiving opening, the thickness of said convex dome portion gradually increasing in all radial directions from said rim to said stoma-receiving opening, adhesive means adhered to at least a portion of said convex dome and having a body-engaging portion substantially covering said upper portion of said pouch, and a soft pliable sealing ring adhered to said convex dome portion adapted to form a seal against the body around the stoma.

* * * * *